(12) United States Patent
Yan et al.

(10) Patent No.: US 8,519,153 B2
(45) Date of Patent: Aug. 27, 2013

(54) COMPOUNDS FOR FLUORESCENT LABELING

(75) Inventors: Hongbin Yan, St. Catharines (CA); Kha Tram, Hamilton (CA)

(73) Assignee: Brock University, St. Catharines (CA)

( * ) Notice: Subject to any disclaimer, the term of this patent is extended or adjusted under 35 U.S.C. 154(b) by 169 days.

(21) Appl. No.: 13/239,705

(22) Filed: Sep. 22, 2011

(65) Prior Publication Data

US 2012/0071644 A1  Mar. 22, 2012

Related U.S. Application Data

(60) Provisional application No. 61/385,193, filed on Sep. 22, 2010.

(51) Int. Cl.
*C07F 5/02* (2006.01)
*C07H 21/04* (2006.01)

(52) U.S. Cl.
USPC ........................................ 548/405; 536/25.32

(58) Field of Classification Search
USPC ........................................ 548/405; 536/25.32
See application file for complete search history.

(56) References Cited

U.S. PATENT DOCUMENTS 5,861,287 A * 1/1999 Metzker et al. ............... 435/91.1
7,671,218 B2   3/2010 Lukhtanov et al.

FOREIGN PATENT DOCUMENTS

CA         2577053 A1   12/2005

OTHER PUBLICATIONS

Tram, Kha; Twohig, Daniel; Yan, Hongbin, "Oligonucleotide Labeling Using BODIPY Phosphoramidite", Nucleosides, Nucleotides and Nucleic Acids, 30:1-11, 2011.
Loudet, Aurore; Burgess, Kevin, "BODIPY Dyes and Their Derivatives: Syntheses and Spectroscopic Properties", Chemical Reviews, 2007, 107 (11), 4891-4932.
Wanninger-Weib et al, "Nucleotide insertion and bypass synthesis of pyrene- and BODIPY-modified oligonucleotides by DNA polymerases", Chem. Commun., 2008. 1443-1445.
Yang, Lijing et al., "Some observations relating to the stability of the BODIPY fluorophore under acidic and basic conditions", Elsevier, Dyes and Pigments 91 (2011) 264-267.

* cited by examiner

*Primary Examiner* — Joseph Kosack
(74) *Attorney, Agent, or Firm* — Bereskin & Parr LLP/S.E.N.C.R.L., s.r.l.; Patricia Folkins (57) ABSTRACT

The present application is directed to compounds of Formula I:

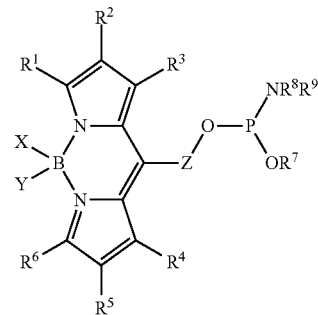

wherein $R^1$-$R^9$, X, Y and Z are as defined in the application, and to the use of the compounds of Formula I, for example, for the fluorescent labeling of oligonucleotides.

20 Claims, 4 Drawing Sheets

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
tcccgccctg tgacatgcat t                                    21

<210> SEQ ID NO 2
<211> LENGTH: 10
<212> TYPE: DNA
<213> ORGANISM: Artificial Sequence
<220> FEATURE:
<223> OTHER INFORMATION: Synthetic

<400> SEQUENCE: 2
tttttttttt                                                 10

COMPOUNDS FOR FLUORESCENT LABELING

CROSS-REFERENCE TO RELATED APPLICATIONS

The present application claims the benefit of priority from co-pending U.S. provisional application No. 61/385,193 filed on Sep. 22, 2010, the contents of which are incorporated herein by reference in their entirety.

INCORPORATION OF SEQUENCE LISTING

A computer readable form of the Sequence Listing "5743-65_SequenceListing.txt" (8,192 bytes), submitted via EFS-WEB and created on Oct. 26, 2011, is herein incorporated by reference.

FIELD OF THE APPLICATION

The present application is directed to novel compounds useful for fluorescent labeling of, for example, oligonucleotides. In particular the present application is directed to BODIPY™ analogues modified to comprise a phosphoramidite and to the use of these compounds to prepare labeled oligonucleotides, for example, using solid phase synthesis.

BACKGROUND OF THE APPLICATION

Fluorescent labeling of oligonucleotides is a technique commonly used in structural and functional studies of oligonucleotides. A wide range of fluorescent reporter groups have been in use, many of these are commercially available (The Handbook, A guide to fluorescent probes and labeling technologies, 10th edition; Haugland, Richard P.; Invitrogen Corp., 2005, pp 315-412). Among these fluorophores, fluorescein, rhodamine and cyanine are the most commonly used. These fluorophores cover a wide range of excitation and emission wavelengths and are in general highly fluorescent; however, most of these fluorophores are charged molecules and the fluorescent properties are often pH and environment dependent. In addition, many of these fluorescent probes are not photostable. The cyanine derivatives Cy3 and Cy5 are the only red-purple emitting fluorophores that are currently available for oligonucleotide labeling through the phosphoramidite chemistry, however, their applications are limited by their (photo)chemical instability. There exists a high demand for such red-purple fluorophores.

Numerous 4,4-difluoro-4-bora-3a,4a-diaza-s-indacene (BODIPY™)

derivatives have been known to possess very high, and some near unity, fluorescent quantum yields that are relatively insensitive to changes in pH and polarity and are stable under many biological conditions (Loudet, A.; Burgess, K. *Chem. Rev.* 2007, 107, 4891; Ulrich, G.; Ziessel, R.; Harriman, A. *Angew. Chem., Int. Ed.* 2008; 47, 1184). These fluorophores are often more photostable than many fluorescein, rhodamine and cyanine analogues. Therefore the BODIPY™ fluorophores have found useful applications in nucleic acid labeling. To date, BODIPY™ labeling of oligonucleotides has been carried out post-synthetically between an amino modifier on oligonucleotides and an activated BODIPY™ carboxylate ester (The Handbook, A guide to fluorescent probes and labeling technologies, 10th edition; Haugland, Richard P.; Invitrogen Corp., 2005, pp 315-412).

U.S. Pat. No. 5,861,287 describes methods for the use of BODIPY™ fluorophore-labelled DNA for dye-primer sequencing. This patent describes a BODIPY™ phosphoramidite derivative where the phosphoramidite is attached at the 3-position of the indacene ring skeleton. Canadian patent application number 2,577,053 describes several fluorescent dyes, including BODIPY™ dyes, substituted by at least one phosphonate group. The only phosphoramidite compounds specifically mentioned contained the phosphoramidite at the 4-position of the indacene ring skeleton. Neither of these documents reports the use of these phosphoramidite BODIPY™ compounds in solid phase oligonucleotide synthesis.

SUMMARY OF THE APPLICATION

The present application describes BODIPY™ analogues in which the phosphoramidite is attached at the meso or 8-position of the indacene ring skeleton and the direct incorporation of these BODIPY™ analogues into oligonucleotides during solid phase synthesis, thereby eliminating the need for post-synthetic conjugation of the fluorophore into the final oligonucleotide. Also described are BODIPY™ analogues possessing a fluorescent emission in the highly demanded red-purple region.

Accordingly, the present application is directed to compounds of Formula I:

wherein
X and Y are independently selected from halogen, OH, $C_{1-20}$alkyl, $C_{2-20}$alkenyl, $C_{2-20}$alkynyl, $C_{1-20}$alkoxy, $C_{2-20}$alkenyloxy, $C_{2-20}$alkynyloxy, $C_{3-20}$cycloalkyl, $C_{3-20}$cycloalkoxy, $C_{6-20}$aryl and $C_{6-20}$aryloxy;
$R^1$, $R^2$, $R^3$, $R^4$, $R^5$ and $R^6$ are independently selected from H, halogen, OPg, $C_{1-20}$alkyl, $C_{2-20}$alkenyl, $C_{2-20}$alkynyl, $C_{3-20}$cycloalkyl, heteroaryl, heterocyclyl and $C_{6-20}$aryl, or any two adjacent $R^1$, $R^2$, $R^3$, $R^4$, $R^5$ and $R^6$ groups are joined together to form a 3-20 membered ring system;
Pg is a suitable protecting group;
$R^7$ is selected from $C_{1-20}$alkyl and $(CH_2)_2CN$;
$R^8$ and $R^9$ are independently selected from $C_{1-20}$alkyl and $C_{3-20}$cycloalkyl;
Z is selected from $C_{1-20}$alkylene and $C_{6-24}$arylene; and each alkyl, alkenyl, alkynyl, cycloalkyl, aryl, heteroaryl and heterocyclyl, alone or part of another group, and the ring system, is unsubstituted or substituted with one or more substituents independently selected from halogen, OPg, $C_{1-6}$alkyl, $C_{1-6}$alkoxy and $C_{6-10}$aryl, or a salt or solvate thereof.

The presence of the phosphoramidite moiety on the 8 (or meso) position advantageously increases the stability of the BODOPY™ core by preventing reactions at this highly reactive site. This characteristic is especially useful for solid phase synthetic reactions.

Accordingly the present application also includes a method of labeling an oligonucleotide comprising performing phosphoramidite-based solid phase synthesis of the oligonucleotide wherein at least one of the reactants is a compound of Formula I as defined above.

The present application also includes a use of a compound of Formula I for labeling an oligonucleotide using phosphoramidite-based solid phase synthesis.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

The application will now be described in greater detail with reference to the drawings in which.

DETAILED DESCRIPTION OF THE APPLICATION (i) Definitions

The following definitions, unless otherwise stated, apply to all aspects and embodiments of the present application.

As used herein, the term "alkyl" includes straight and branched chain hydrocarbons. For example, alkyl groups include methyl, ethyl, propyl, isopropyl, butyl, isobutyl, sec-butyl, t-butyl, pentyl and the like. As a further example, "$C_{1-20}$" when used as a prefix to alkyl means a straight or branched carbon chain group having 1, 2, 3, 4, 5, 6, 7, 8, 9, 10, 11, 12, 13, 14, 15, 16, 17, 18, 19 or 20 carbon atoms.

As used herein, the term "alkenyl" includes straight and branched chain hydrocarbons comprising at least one, for example 1 to 8, 1 to 6, 1 to 5, or 1 to 4, or 1 to 3, double bonds. For example, alkenyl groups include vinyl, propenyl, isopropenyl, butenyl, isobutenyl, pentenyl and the like. As a further example, "$C_{2-20}$" when used as a prefix to alkenyl means a straight or branched carbon chain group having 2, 3, 4, 5, 6, 7, 8, 9, 10, 11, 12, 13, 14, 15, 16, 17, 18, 19 or 20 carbon atoms.

As used herein, the term "alkynyl" includes straight and branched chain hydrocarbons comprising at least one, for example 1 to 8, 1 to 6, 1 to 5, or 1 to 4, or 1 to 3, triple bonds. For example, alkynyl groups include acetylenyl, propargyl, butynyl, pentynyl and the like. As a further example, "$C_{2-20}$" when used as a prefix to alkynyl means a straight or branched carbon chain group having 2, 3, 4, 5, 6, 7, 8, 9, 10, 11, 12, 13, 14, 15, 16, 17, 18, 19 or 20 carbon atoms.

The term "cycloalkyl" as used herein means a saturated monocyclic hydrocarbon ring or a saturated polycyclic hydrocarbon ring system and includes, for example, cyclopropyl, cyclobutyl, cyclopentyl, cyclohexyl, cycloheptyl, adamantyl and the like. As a further example, "$C_{3-20}$" when as a prefix to cycloalkyl means a cycloalkyl group having 3, 4, 5, 6, 7, 8, 9, 10, 11, 12, 13, 14, 15, 16, 17, 18, 19 or 20 carbon atoms.

The term "aryl" as used herein means a monocyclic hydrocarbon ring or polycyclic hydrocarbon ring system containing at least one aromatic ring and includes phenyl, naphthyl, anthracenyl, 1,2-dihydronaphthyl, 1,2,3,4-tetrahydronaphthyl, fluorenyl, indanyl, indenyl and the like. As a further example, "$C_{6-20}$" when used as a prefix to aryl means an aryl group having 3, 4, 5, 6, 7, 8, 9, 10, 11, 12, 13, 14, 15, 16, 17, 18, 19 or 20 carbon atoms.

The term "heteroaryl" as used herein means a monocyclic ring or a polycyclic ring system containing 5, 6, 7, 8, 9, 10, 11, 12, 13, 14, 15, 16, 17, 18, 19 or 20 atoms, of which one or more, for example 1 to 8, 1 to 6, 1 to 5, or 1 to 4, of the atoms are a heteromoiety selected from O, S, NH and $NC_{1-6}$alkyl, with the remaining atoms being C, CH or $CH_2$, said ring system containing at least one aromatic ring. Examples of heteroaryl groups, include, but are not limited to furanyl, thiophenyl, pyrrolyl, imidazolyl, pyrazolyl, triazolyl, oxazolyl, isoxazolyl, thiazolyl, isothiazolyl, oxadiazolyl, tetrazolyl, oxatriazolyl, isoxazinyl, pyridinyl, pyridazinyl, pyrimidinyl, pyrazinyl, triazinyl, benzofuranyl, isobenzofuranyl, benzothiophenyl, indolyl, isoindolyl; quinolinyl, isoquinolinyl, benzodiazinyl, pyridopyridinyl, acridinyl, xanthenyl and the like.

The term "heterocyclyl" as used herein means a saturated or unsaturated monocyclic ring or a saturated or unsaturated polycyclic ring system containing 3, 4, 5, 6, 7, 8, 9, 10, 11, 12, 13, 14, 15, 16, 17, 18, 19 or 20 atoms, of which one or more, for example 1 to 8, 1 to 6, 1 to 5, or 1 to 4, of the atoms are a heteromoiety selected from O, S, NH and $NC_{1-6}$alkyl, with the remaining atoms being C, CH or $CH_2$. Examples of heterocyclyl groups, include, but are not limited to aziridinyl, azetidinyl, pyrrolidinyl, pyrrolinyl, 2H-pyrrolyl, 3H-pyrrolyl, piperidinyl, dihydropyridinyl, tetrahydropyridinyl, azepinyl, oxiranyl, oxetanyl, oxolanyl (tetrahydrofuranyl), oxolyl (dihydrofuranyl), oxanyl (tetrahydropyranyl), dihydropyranyl, pyranyl, oxepinyl, thiiranyl, thietanyl, thiolanyl (tetrahydrothiophenyl), thianyl (tetrahydrothiopyranyl), thiepanyl, dioxolanyl, dioxanyl, dioxepanyl, trioxanyl, imidazolidinyl, pyrazolidinyl (diazolidinyl), imidazolinyl, pyrazolinyl (dihydropyrazolyl), piperazinyl, tetrahydrooxazolyl, dihydrooxazolyl, tetrahydroisoxazolyl, dihydroisoxazolyl, morpholinyl, tetrahydrooxazinyl, dihydrooxazinyl, oxazinyl, thiazolinyl, thiazolidinyl, thiomorpholinyl, oxadiazinyl, oxathiolyl and oxathianyl (thioxanyl), oxathiazinyl and the like.

The term "halo" as used herein means halogen and includes chloro, fluoro, bromo and iodo. The term "halide" as used herein means a halogen anion, including $Cl^-$, $Br^-$, $F^-$ and $I^-$.

The suffix "ene" added on to any of the claimed groups means that the group is divalent, i.e. inserted between two other groups. When the group is a ring system, the two other groups may be located at any location on the ring system, including at adjacent and non-adjacent nodes. For example, if the group is phenylene, the two other groups may be located at positions 1 and 2, 1 and 3 or 1 and 4 of the phenyl ring.

The term "ring system" as used herein refers to any type of cyclic structure that comprises one or more rings and any type of saturation and optionally includes, where indicated, heteromoieties or metals. Ring systems formed between two adjacent R groups, include within the system the atoms to which the R groups are attached and any atoms linking the atoms to which the R groups are attached.

The term "polycyclic" as used herein refers to a cyclic structure that comprises more than one ring, for example 2, 3, 4, or 5 rings. The rings may be linked through a single bond, a single atom (spirocyclic) or through two atoms (fused and bridged).

The term "joined together" as used herein means that two substituents are linked together via a linker grouping to form a ring system. The linker grouping comprises at least one atom but may also comprise several atoms, for example up to 20 atoms, which optionally includes monocyclic rings and polycyclic ring systems.

The term "fluoro-substituted" as used herein means that one or more, including all, of the hydrogens on a group are replaced with fluorine. Examples of a fluoro-substituted alkyl group are $CF_3$, $CF_2CF_3$, $CH_2CF_3$ and the like. Examples of fluoro-substituted aryl groups are $C_6F_5$, $C_6H_4F$ and the like.

In certain embodiments of the application, the compounds described herein may have at least one asymmetric centre. Where compounds possess more than one asymmetric centre, they may exist as diastereomers. It is to be understood that all such isomers and mixtures thereof in any proportion are encompassed within the scope of the present application. It is to be understood that while the stereochemistry of the compounds may be as shown in any given compound listed herein, such compounds may also contain certain amounts (e.g. less than 20%, suitably less than 10%, more suitably less than 5%) of compounds of the application having alternate stereochemistry.

During any of the processes for preparation of the compounds of the present application, it may be necessary and/or desirable to protect sensitive or reactive groups on any of the molecules concerned. This is achieved by means of conventional protecting groups. The protecting groups may be removed at a convenient subsequent stage using methods known from the art.

The terms "protective group" or "protecting group" or "Pg" or the like as used herein refer to a chemical moiety which protects or masks a reactive portion of a molecule to prevent side reactions in those reactive portions of the molecule, while manipulating or reacting a different portion of the molecule. After the manipulation or reaction is complete, the protection group is typically removed under conditions that do not destroy or decompose the molecule. Many conventional protecting groups are known in the art for example as described in "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, $3^{rd}$ Edition, 1999. These include but are not limited to t-butyloxycarbonyl (t-Boc), tosylate (Ts), mesylate (Ms), brosylate, t-butyldimethylsilyl (TBDMS), tert-butyldiphenylsilyl (TBDPS), triflate (Tf), benzyl (Bn), allyl, fluorenylmethyloxycarbonyl (Fmoc), $C_{1-16}$-acyl, acetal, DMTr (dimethoxytrityl) and counterions and the like.

The term "leaving group" as used herein refers to a group that is readily displaceable by a nucleophile, for example, under nucleophilic substitution reaction conditions. Examples of suitable leaving groups include, halogen, OMs, OTs, ONs, OTf, Bn, $OC_{1-6}$acyl, $OC_{1-16}$alkyl, alkylsulphonyoxyl and the like.

The term "salt" as used herein means any organic or inorganic salt of any neutral compound. If the compound comprises a basic group, for example an amine, an acid addition salt is formed by adding a suitable acid. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, oxalic, citric, ascorbic, maleic, benzoic, phenylacetic, cinnamic and salicylic acids, as well as sulfonic acids such as p-toluene sulfonic and methanesulfonic acids. If the compound comprises an acidic group, for example a carboxylic acid, a basic addition salt is formed by adding a suitable base. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline, alkylammonias or ammonia. Such salts may exist in either a hydrated, solvated or substantially anhydrous form. The selection of the appropriate salt will be known to one skilled in the art.

The formation of a desired compound salt is achieved using standard techniques. For example, the neutral compound is treated with an acid or base in a suitable solvent and the formed salt is isolated by filtration, extraction or any other suitable method The term "solvate" as used herein means a compound, or a salt of a compound, wherein molecules of a suitable solvent are incorporated in the crystal lattice. When water is the solvent, the molecule is referred to as a "hydrate". The formation of solvates of compounds will vary depending on the compound and the solvate. In general, solvates are formed by dissolving the compound in the appropriate solvent and isolating the solvate by cooling or using an antisolvent. The solvate is typically dried or azeotroped under ambient conditions.

As used herein, unless otherwise noted, the term "antisolvent" refers to a solvent which does not dissolve a specific substance and is added to a solution of said substance, directly or by vapor diffusion, to cause precipitation of said substance.

The term "suitable" as used herein means that the selection of the particular compound, group, atom or conditions would depend on the specific synthetic manipulation to be performed, and the identity of the molecule(s) to be transformed, but the selection would be well within the skill of a person trained in the art. All synthetic steps described herein are to be conducted under conditions sufficient to provide the product shown. Unless otherwise indicated, a person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The products of the processes of the application may be isolated according to known methods, for example, the compounds may be isolated by evaporation of the solvent, by filtration, centrifugation, chromatography or other suitable method.

One skilled in the art will recognize that where a reaction step of the present application is carried out in a variety of solvents or solvent systems, said reaction step may also be carried out in a mixture of the suitable solvents or solvent systems.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

(ii) Compounds of the Application

The present application is directed to a compound of Formula I:

(I)

wherein
X and Y are independently selected from halogen, OH, $C_{1-20}$alkyl, $C_{2-20}$alkenyl, $C_{2-20}$alkynyl, $C_{1-20}$alkoxy, $C_{2-20}$alkenyloxy, $C_{2-20}$alkynyloxy, $C_{3-20}$cycloalkyl, $C_{3-20}$cycloalkoxy, $C_{6-20}$aryl and $C_{6-20}$aryloxy;
$R^1$, $R^2$, $R^3$, $R^4$, $R^5$ and $R^6$ are independently selected from H, halogen, OPg, $C_{1-20}$alkyl, $C_{2-20}$alkenyl, $C_{2-20}$alkynyl, $C_{3-20}$cycloalkyl, heteroaryl, heterocyclyl and $C_{6-20}$aryl, or any two adjacent $R^1$, $R^2$, $R^3$, $R^4$, $R^5$ and $R^6$ groups are joined together to form a 3-20 membered ring system;
Pg is a suitable protecting group;
$R^7$ is selected from $C_{1-20}$alkyl and $(CH_2)_2CN$;
$R^8$ and $R^9$ are independently selected from $C_{1-20}$alkyl and $C_{3-20}$cycloalkyl;
Z is selected from $C_{1-20}$alkylene and $C_{6-24}$arylene; and
each alkyl, cycloalkyl, aryl, heteroaryl and heterocyclyl, alone or part of another group, and the ring system, is unsubstituted or substituted with one or more substituents independently selected from halogen, OPg, $C_{1-6}$alkyl, $C_{1-6}$alkoxy and $C_{6-10}$aryl,
or a salt or solvate thereof.

In the compounds of Formula I, X and Y are independently selected from halogen, $C_{1-20}$alkyl, $C_{2-20}$alkenyl, $C_{2-20}$alkynyl, $C_{1-20}$alkoxy, $C_{2-20}$alkenyloxy, $C_{2-20}$alkynyloxy, $C_{3-20}$cycloalkyl, $C_{3-20}$cycloalkoxy, $C_{6-20}$aryl and $C_{6-20}$aryloxy, and each alkyl, cycloalkyl, aryl, heteroaryl and heterocyclyl, alone or part of another group, is unsubstituted or substituted with one or more substituents independently selected from halogen, $C_{1-6}$alkyl, $C_{1-6}$-alkoxy, and $C_{6-10}$aryl. In an embodiment of the application, X and Y are independently selected from halogen and $C_{1-10}$alkoxy, where the alkoxy group is optionally fluoro-substituted. In a further embodiment, that X and Y are independently selected from F and $C_{1-6}$alkoxy, where the alkoxy group is optionally fluoro-substituted. In another embodiment X and Y are independently selected from F, methoxy, ethoxy, trifluoromethoxy and pentafluoroethoxy. In another embodiment X and Y are both F or are both methoxy.

In the compounds of Formula I, $R^1$, $R^2$, $R^3$, $R^4$, $R^5$ and $R^6$ are independently selected from H, halogen, OPg, $C_{1-20}$alkyl, $C_{2-20}$alkenyl, $C_{2-20}$alkynyl, $C_{3-20}$cycloalkyl, heteroaryl, heterocyclyl and $C_{6-20}$aryl, or any two adjacent $R^1$, $R^2$, $R^3$, $R^4$, $R^5$ and $R^6$ groups are joined together to form a 3-20 membered ring system, and each alkyl, cycloalkyl, aryl, heteroaryl and heterocyclyl, alone or part of another group, and the ring system, is unsubstituted or substituted with one or more substituents independently selected from halogen, $C_{1-6}$alkyl, $C_{1-6}$alkoxy and $C_{6-10}$aryl. In an embodiment of the application, $R^1$, $R^2$, $R^3$, $R^4$, $R^5$ and $R^6$ are independently selected from H, halogen and $C_{1-10}$alkyl, or any two adjacent $R^1$, $R^2$, $R^3$, $R^4$, $R^5$ and $R^6$ groups are joined together to form a 5-6-membered ring, where the alkyl groups are optionally fluoro-substituted. In another embodiment, $R^1$, $R^2$, $R^3$, $R^4$, $R^5$ and $R^6$ are independently selected from H, halogen and $C_{1-6}$alkyl, or any two adjacent $R^1$, $R^2$, $R^3$, $R^4$, $R^5$ and $R^6$ groups are joined together to form a 5-6-membered carbocyclic ring, where the alkyl groups are optionally fluoro-substituted. In yet another embodiment, $R^1$, $R^2$, $R^3$, $R^4$, $R^5$ and $R^6$ are independently selected from H and $C_{1-6}$alkyl or any two adjacent $R^1$, $R^2$, $R^3$, $R^4$, $R^5$ and $R^6$ groups are joined together to form a 5-6-membered carbocyclic aromatic ring, where the alkyl groups are optionally fluoro-substituted. In yet another embodiment, $R^1$, $R^3$, $R^4$ and $R^6$ are independently selected from methyl, trifluoromethyl, ethyl and pentafluoroethyl and $R^2$ and $R^5$ are both H.

It is an embodiment of the present application that one of $R^1$, $R^2$, $R^3$, $R^4$, $R^5$ and $R^6$ is OPg. In this embodiment, the compounds of Formula I can be incorporated into any site of an oligonucleotide sequence. In an embodiment, the suitable Pg is an acid labile protecting group such as dimethoxytrityl (DMTr).

In the compounds of Formula I, $R^7$ is selected from $C_{1-20}$alkyl and $(CH_2)_2CN$; and is unsubstituted or substituted with one or more substituents independently selected from halogen, $C_{1-6}$alkyl, $C_{1-6}$alkoxy and $C_{6-10}$aryl, and n is 1 to 6. In an embodiment of the application, $R^7$ is selected from $C_{1-6}$alkyl and $(CH_2)_2CN$. In a further embodiment, $R^7$ is selected from methyl and $(CH_2)_2CN$.

In the compounds of Formula I, $R^8$ and $R^9$ are independently selected from $C_{1-20}$alkyl and $C_{3-20}$cycloalkyl, and each alkyl and cycloalkyl, is unsubstituted or substituted with one or more substituents independently selected from halogen, $C_{1-6}$alkyl, $C_{1-6}$alkoxy and $C_{6-10}$aryl. In an embodiment of the application, $R^8$ and $R^9$ are independently $C_{1-6}$alkyl that is optionally fluoro-substituted. In a further embodiment $R^8$ and $R^9$ are independently selected from are both methyl, trifluoromethyl, ethyl or pentafluoroethyl.

In the compounds of Formula I, Z is selected from $C_{1-20}$alkylene and $C_{6-24}$arylene, and each alkyl and aryl, is unsubstituted or substituted with one or more substituents independently selected from halogen, OPg, $C_{1-6}$alkyl, $C_{1-6}$alkoxy and $C_{6-10}$aryl. In an embodiment of the application Z is selected from $C_{1-10}$alkylene, phenylene and bi-phenylene, and each alkyl and phenyl, is unsubstituted or substituted with one or more substituents independently selected from OPg and $C_{1-6}$alkyl. In a further embodiment, Z is $C_{3-8}$alkylene that is unsubstituted or substituted with one or more substituents independently selected from OPg and $C_{1-6}$alkyl. When Z is substituted with OPg, the compounds of Formula I can be incorporated into any site of an oligonucleotide sequence. In an embodiment, the Pg is an acid labile protecting group such as dimethoxytrityl (DMTr).

In an embodiment, the compound of Formula I is selected from:

Synthesis of the compounds of the present application may be performed, for example, using methods known in the art. See, for example, Loudet, A.; Burgess, K. Chem. Rev. 2007, 107, 4891, the contents of which are incorporated herein by reference in their entirety. The compounds of the present application may also be prepared using the methods described herein.

(iii) Methods and Uses for the Compounds of Formula I

The BODIPY™ phosphoramidites of the present application were incorporated into oligonucleotides at the 5'-termini as a fluorescent labeling agent using solid phase synthesis. Due to the advantages of the BODIPY™ fluorophores, this approach provides a useful alternative to other commercially available fluorophores for DNA/RNA labeling. The presence of the phosphoramidite moiety on the 8 (or meso) position advantageously increases the stability of the BODOPY™ core by preventing reactions at this highly reactive site under solid phase synthesis reaction conditions. Further, phenyl substituted analogs, such as compound I(c) fluoresce in the red-purple region making them a highly desirable fluorphores since very few compounds exist with fluorescent properties in this region. Compounds of Formula I wherein at least one of $R^1$, $R^2$, $R^3$, $R^4$, $R^5$ and $R^6$ is OPg can be incorporated at any site of the oligonucleotide, including the 3' or 5' end and any site in between.

Accordingly the present application also includes a method of labeling an oligonucleotide comprising performing phosphoramidite-based solid phase synthesis of the oligonucleotide wherein at least one of the reactants is a compound of Formula I as defined above.

The present application also includes a use of a compound of Formula I for labeling an oligonucleotide using phosphoramidite-based solid phase synthesis.

The term "oligonucleotide" as used herein refers to all such compounds including deoxyribonucleotides (DNA) and ribonucleotides (RNA) and analogues thereof amenable to phosphoramidite-based solid phase synthesis.

EXAMPLES

The following Examples are set forth to aid in the understanding of the application, and are not intended and should not be construed to limit in any way the application set forth in the claims which follow thereafter.

Instrumentation

Melting points were measured with a Stuart Scientific melting pointing apparatus and are uncorrected. $^1$H NMR spectra were measured at 300 and 600 MHz with Bruker AV300, and AV600 spectrometers; tetramethylsilane was used as an internal standard; J values are given in Hz. $^{13}$C NMR spectra were measured at 75.5 or 150.9 MHz with the same spectrometers. $^{31}$P NMR spectra were measured at 121.5 or 242.9 MHz with the same spectrometers, and were referenced to external 85% $H_3PO_4$. Chemical shifts are given in ppm. Low and high resolution mass spectra were obtained with Kratos Concept 1S high resolution mass spectrometer using electron impact or fast atom bombardment sources interfaced with DART 32 bit acquisition system through a Sun Sparcstation 10 and Mach 3 software. Bruker HCT Proteineer with electrospray may be interfaced with an Agilent 1100 series LC system with built-in auto-sampler and diode array detector were used for LC-MS. UV/Vis spectrums were obtained using a Thermospectronic/Unicam UV/Vis spectrometer configured to the Vision32 software. Fluorimetric data were gathered using QuantaMaster model QM-2001-4 cuvette-based L-format scanning spectrofluorometer from Photon Technology International (PTI) interfaced with FeliX32 software.

Chromatography

Merck silica gel Art 7734-3 was used for flash column chromatography.

Anion exchange chromatography (HPLC) was carried out using a Dionex ICS 3000 System on a 4×250 mm Dionex DNA Pac100 column.

Chemicals and Solvents

Suitably-protected nucleoside phosphoramidites and solid supports were purchased from Glen Research. The other chemicals were purchased from Aldrich or Alfa Aesar and used without further purification unless stated otherwise.

Acetonitrile, diethyl ether, and dichloromethane were purified by Pure-Solv Solvent Purification Systems (Innovative Technology), and stored over activated 4 Å molecular sieves.

Pyridine and triethylamine were dried by heating, under reflux, over calcium hydride and then distilled. 1,8-Diazabicyclo[5.4.0]undec-7-ene was dried by heating with calcium hydride at 60° C. and then distilled under reduced pressure.

Example 1

4,4-Difluoro-4-bora-1,3,5,7-tetramethyl-8-(5-bromopentyl)-3a,4a-diaza-s-indacene A solution of 6-bromohexanoyl chloride (0.56 ml, 3.7 mmol) in dry dichloromethane (25 ml) was added dropwise over a period of 5 min to a solution of 2,4-dimethylpyrrole (1.0 ml, 9.7 mmol) in dry dichloromethane (10 ml). The mixture was heated under reflux for 3 h and then concentrated to dryness under reduced pressure. The residue was dissolved in dry dichloromethane (10 ml) followed by addition of dry hexane (100 ml). After the mixture was left at −4° C. overnight, the supernatant was decanted and the residue was washed with cold hexane (2×20 ml) and then dissolved in dry toluene (30 ml). Dry triethylamine (1.0 ml, 7.2 mmol) was added and the reaction mixture was stirred for 15 min. Boron trifluoride diethyl etherate (1.2 ml, 9.6 mmol) was then added and the mixture was heated at 40° C. for 3 h. Upon cooling to room temperature, the products were successively washed with water (30 ml) and brine (3×30 ml). The organic layer was dried ($MgSO_4$) and concentrated under reduced pressure to give a dark red oil. The mixture was purified by column chromatography on silica gel. The appropriate fractions, which were eluted with dichloromethane-hexane (1:1 v/v), were pooled and concentrated under reduced pressure to yield the title compound as a bright orange solid (0.78 g, 62%).

HR-FAB found $M^+$=396.11746, $C_{18}H_{24}BBrF_2N_2^+$ requires 396.11840

Example 2

4,4-Difluoro-4-bora-1,3,5,7-tetramethyl-8-(5-hydroxypentyl)-3a,4a-diaza-s-indacene

4,4-Difluoro-4-bora-1,3,5,7-tetramethyl-8-(5-bromopentyl)-3a,4a-diaza-s-indacene (0.20 g, 0.60 mmol) and potassium acetate (0.17 g, 1.72 mmol) were purged with nitrogen in a septum-capped flask. The solids were then dissolved in dry DMF (10 ml) and stirred at 50° C. for 3 d. After the products were cooled to room temperature, ethyl acetate (50 ml) was added and the resulting mixture was washed successively with distilled water (50 ml) and brine (3×50 ml). The organic layer was dried ($MgSO_4$) and concentrated under reduced pressure and the products (4,4-difluoro-4-bora-1,3,5,7-tetramethyl-8-(5-acetoxypentyl)-3a,4a-diaza-s-indacene) were used for the next step without further purification.

The residue above was dissolved in a mixture of THF-methanol (10 ml, 2:8 v/v) and sparged with nitrogen for 15 min. In a separate flask, lithium hydroxide monohydrate (41 mg, 0.98 mmol) was dissolved in distilled water (5 ml) and sparged with nitrogen for 15 min. The latter solution was then added dropwise to the former over 5 min. After 3 h, the products were concentrated to dryness under reduced pressure and the residue was purified by column chromatography on silica gel. The appropriate fractions, which were eluted with dichloromethane-methanol (98:2 v/v) were combined and concentrated under reduced pressure to give the title compound as a bright orange solid (98 mg, 50%).

HR-FAB found $M^+$=334.20448, $C_{18}H_{25}BF_2N_2O^+$ requires 334.20280

Example 3

4,4-Dimethoxy-4-bora-1,3,5,7-tetramethyl-8-(5-bromopentyl)-3a,4a-diaza-s-indacene 4,4-Difluoro-4-bora-1,3,5,7-tetramethyl-8-(5-bromopentyl)-3a,4a-diaza-s-indacene (25 mg, 0.075 mmol) and aluminum chloride (13 mg, 0.097 mmol) were dissolved in dry dichloromethane (10 ml) and heated to 45° C. for 5 min. The reaction mixture was cooled to room temperature followed by addition of dry methanol (5 ml). After 10 min, the products were concentrated to dryness under reduced pressure. The residue was purified by column chromatography on silica gel. The appropriate fractions, which were eluted with dichloromethane-methanol (98:2 v/v) were combined and evaporated under reduced pressure to give the title compound as an orange solid (26 mg, 83%).

Example 4

Di-Isoindole Analogues

Using the procedure described in Example 1, the above compound was prepared by replacing 2,4-dimethylpyrrole with 1-phenylisoindole. The desired compound was obtained as a bright green solid (0.797 g, 48%).

EI found M$^+$=593, $C_{34}H_{28}BBrF_2N_2^+$ 593.

Example 5

Phosphoramidite of 4,4-Difluoro-4-bora-1,3,5,7-tetramethyl-8-(5-hydroxypentyl)-3a,4a-diaza-s-indacene (Compound I(a))

4,4-Difluoro-4-bora-1,3,5,7-tetramethyl-8-(5-hydroxypentyl)-3a,4a-diaza-s-indacene (0.40 g, 1.20 mmol) was co-evaporated with dry toluene (7 ml) and redissolved in dry THF (10 ml). N,N-Diisopropylethylamine (0.46 ml, 2.64 mmol) followed by N,N-diisopropyl phosphochloridite (0.45 g, 1.92 mmol) were added to the reaction mixture and the reaction was allowed to proceed for 30 min at room temperature. The products were then concentrated under reduces pressure and purified by column chromatography on silica gel. The appropriate fractions, which were eluted with acetone-hexane-triethylamine (20:78:2 v/v) were combined and evaporated under reduced pressure to yield the phosphoramidite as a bright orange oil (0.33 g, 52%).

$\delta_P$[CDCl$_3$, 121.5 MHz]: 149.9

In a like manner, the following additional phosphoramidites of Formula I can be prepared:

Example 6

Solid Phase Synthesis of BODIPY Labeled Oligonucleotides

Thymidine immobilized on the Q-linker (Glen Research) was used as the solid support. Solid phase synthesis was performed on ABI 3400 DNA synthesizer. Standard ABI 1.0 µmol DNA synthesis cycle was used for the Solid phase synthesis of BODIPY™ labeled oligonucleotides. All phosphoramidites were prepared as 0.1 M solutions in acetonitrile. S-Ethyltetrazole (0.25 M in acetonitrile) was used as the activator and coupling time of 20 s was used. Trichloroacetic acid solution (3% in dichloromethane) was used for detritylation (110 s continuous detritylation).

Example 7

Deprotection of BODIPY-Labeled Oligonucleotides

The product from solid phase synthesis was dried and emptied into an eppendorf tube, and incubated with concentrated aqueous ammonia at room temperature for 2 h. After centrifugation at 10,000 rpm for 5 min, the supernatant was collected and lyophilized to give fully-deprotected BODIPY™-labeled oligonucleotides.

Example 8

Relative Fluorescent Quantum Yield Determination

Five solutions with increasing concentrations (BODIPY™ in methanol and fluorescein in 0.1 M NaOH) were prepared and corresponding absorbance measured at 497 and 492 nm, respectively. The concentrations of these solutions were kept low so that the absorbance does not exceed 0.10. The integrated fluorescence intensities of the solutions were measured on a fluorimeter. Graphs of integrated fluorescence intensity vs absorbance were plotted for both BODIPY™ and fluorescein, and the gradients of the linear plots were used for the calculation of fluorescence quantum yields.

Discussion

Figure 1:
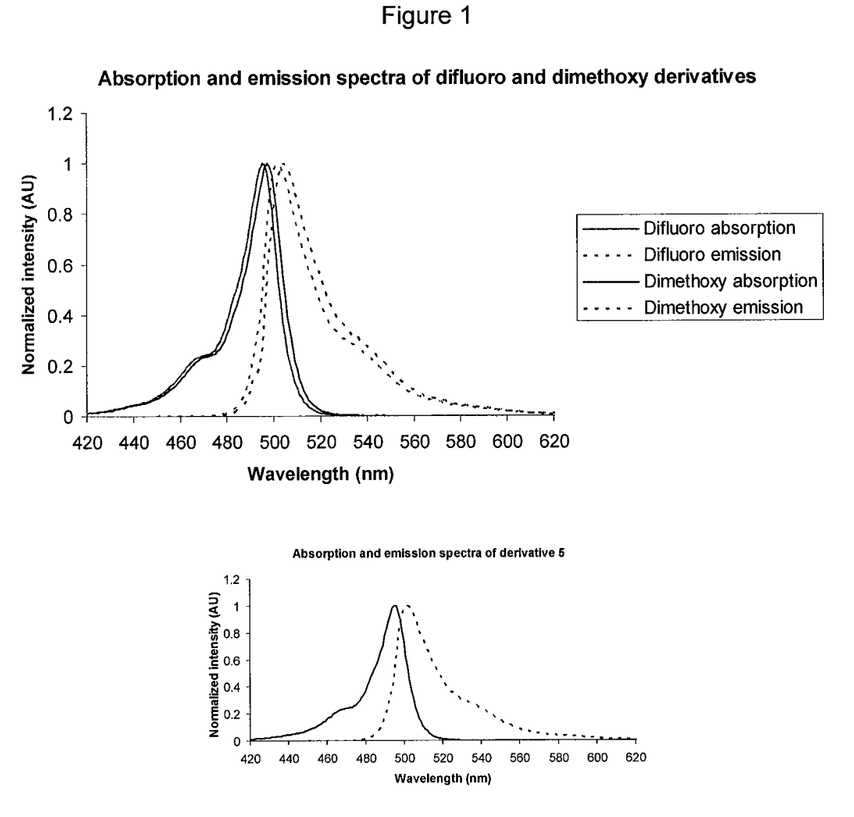
FIG. 1 shows absorption and emission spectra of 4,4-difluoro-4-bora-1,3,5,7-tetramethyl-8-(5-bromopentyl)-3a,4a-diaza-s-indacene and its 4,4-dimethoxy derivative.

As shown in FIG. 1, 4,4-difluoro-4-bora-1,3,5,7-tetramethyl-8-(5-bromopentyl)-3a,4a-diaza-s-indacene showed a typical BODIPY UV and fluorescent profile, with a Stoke's shift of 7 nm. The relative fluorescent quantum yield of 5 was determined to be 0.98 (in methanol) using the literature procedure (Principles of Fluorescence Spectroscopy, 3rd edition. Lacowicz, J. R.; Springer US: 2006, pp 54-55) with fluorescein as the standard ($\phi f$=0.95).

In order for the BODIPY building blocks to be incorporated by the phosphoramidite chemistry-based solid phase synthesis, it is desirable that they be stable during chain assembly and subsequent deprotection conditions once the desired sequence is assembled on the solid support. One such key deprotection step involves a treatment with a base to free the oligonucleotide products from the solid support. This treatment releases the oligonucleotide from solid support, and removes the acyl protecting groups on the base residues and O-cyanoethyl from the internucleotide phosphate linkages. A common deprotection condition is to incubate the immobilized oligonucleotide product in concentrated aqueous ammonia solution at 55° C. for 12 h.

The 4,4-dimethoxy-4-bora-1,3,5,7-tetramethyl-8-(5-bromopentyl)-3a,4a-diaza-s-indacene appeared not to be indefinitely stable in air. Therefore 4,4-difluoro-4-bora-1,3,5,7-tetramethyl-8-(5-bromopentyl)-3a,4a-diaza-s-indacene analogue was initially used for transformation into a phosphoramidite for incorporation into oligonucleotides.

Figure 2:
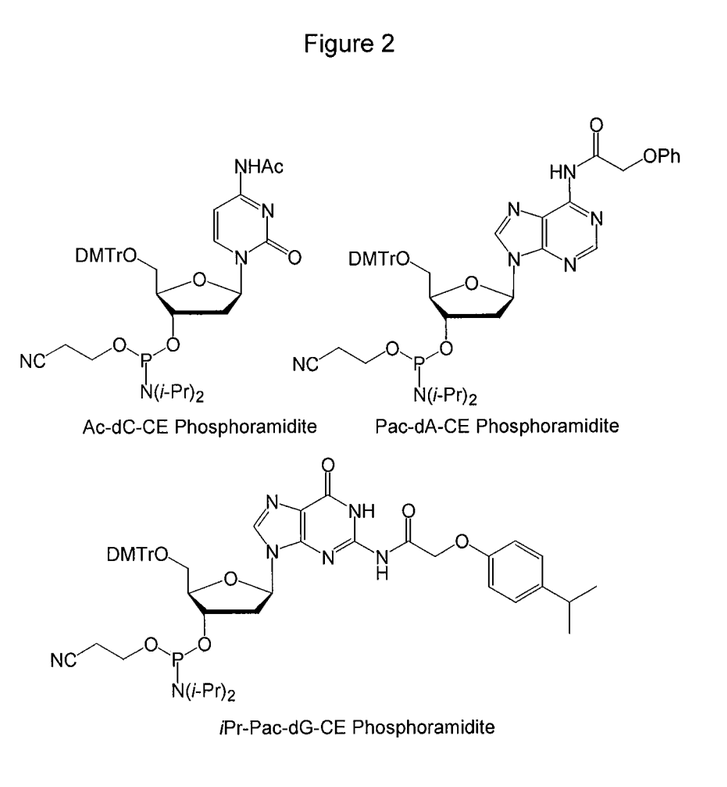
FIG. 2 shows the chemical structures of ultramild phosphoramidites used in solid phase oligonucleotide synthesis (DMTr: dimethoxytrityl).

The Q-linker (Pon, R. T.; Yu, S, *Nucleic Acids Res.* 1997, 25, 3629) and 5'-O-dimethoxytrityl ultramild nucleoside phosphoramidites were used for solid phase oligonucleotide synthesis (FIG. 2, thymidine phosphoramidite is not protected on thymine). Use of the Q-linker and the ultramild phosphoramidites allows for fast cleavage of oligonucleotide products from the solid support and deprotection of base acyl protecting groups, respectively, under basic conditions, and contributing to the integrity of the BODIPY™ core structure.

Solid phase syntheses of oligodeoxyribonucleotides labeled with BODIPY™ at the 5'-end were performed on ABI 3400 DNA synthesizer. Built-in ABI 1.0 µmol DNA synthesis cycle was used. All phosphoramidites were prepared as 0.10 M solution in acetonitrile. S-Ethyltetrazole (0.25 M in acetonitrile) was used as activator and coupling time of 20 s was used. Trichloroacetic acid solution (3% in dichloromethane) was used for detritylation (110 s continuous flow through the column). After chains are assembled, the products were deprotected (cleavage from solid support and removal of base protecting groups) by incubation in concentrated ammonium hydroxide solution at room temperature for up to 2 h. The supernatants were lyophilized and analyzed by anion exchange chromatography.

Figure 3A:
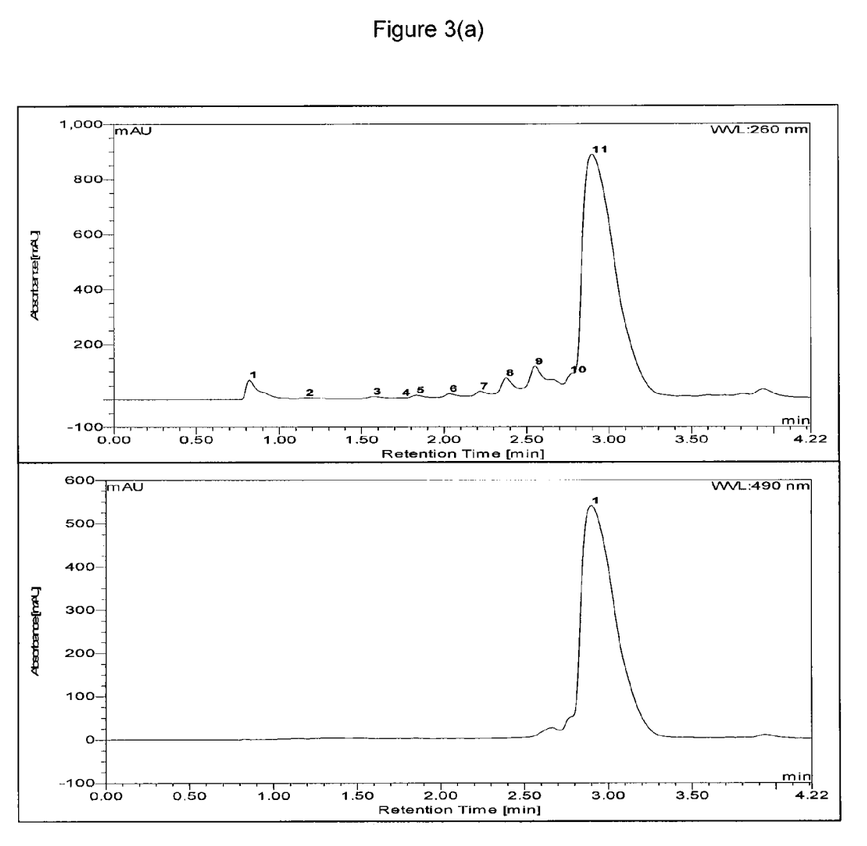
FIG. 3 shows anion exchange HPLC chromatograms of oligonucleotides labeled with BODIPY™ at the 5'-end. a). Sequence A. Top and bottom profiles monitored at 260 and 490 nm, respectively; b). Sequence B. Top and bottom profiles monitored at 260 and 490 nm, respectively.
Figure 3B:
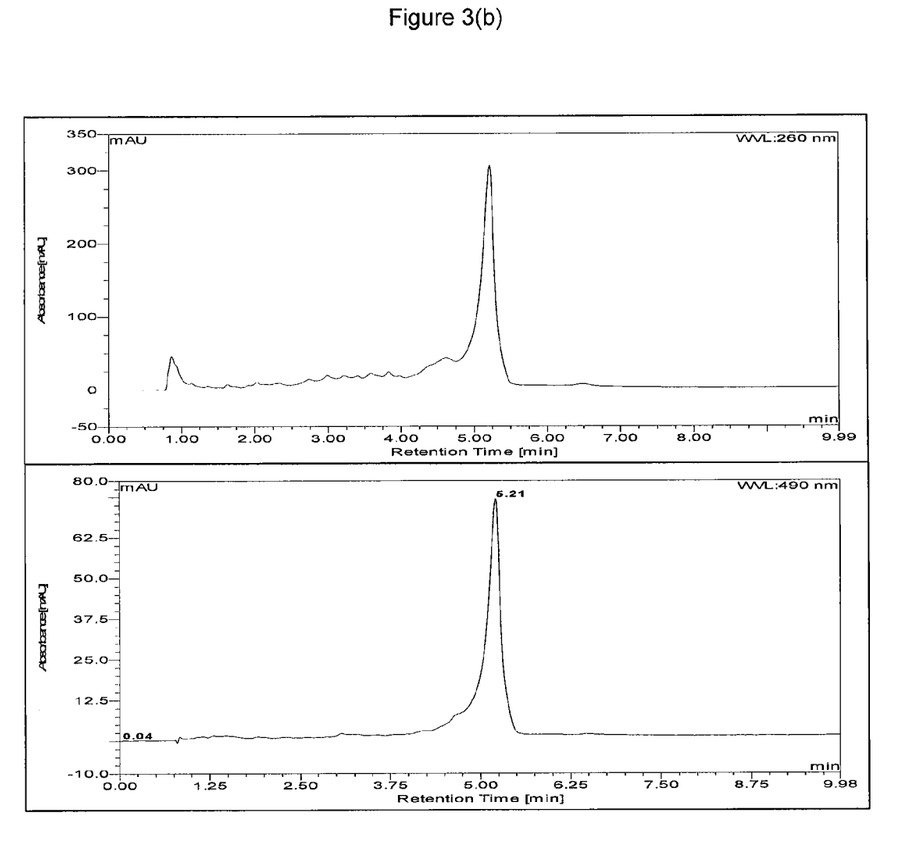

Two sequences with BODIPY labeling at the 5'-termini were synthesized (sequence A: 5'-BODIPY-T$_{10}$-3' (SEQ ID NO: 1); sequence B: 5'-BODIPY-d[TCCCGCCTGTGACATGCATT]-3' (SEQ ID NO: 2)). As can be seen in the anion exchange HPLC chromatograms of the fully deprotected oligonucleotides (FIG. 3), both sequences were successfully labeled with BODIPY at the 5'-end. Since 4,4-difluoro-4-bora-1,3,5,7-tetramethyl-8-(5-bromopentyl)-3a,4a-diaza-s-indacene derivative shows maximal absorption at 495 nm where nucleosides do not absorb, the HPLC profiles clearly indicated that the major component that appears in the profile monitored at 260 nm is labeled with BODIPY. Both fully deprotected products were analyzed by electrospray (ESI) mass spectroscopy in the negative mode, and the observed masses of both sequences were in good agreement with calculated values (Table 2).

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

| Compound | Maximal absorption wavelength $\lambda_{max}^{ab}$ (nm) | Maximal emission wavelength $\lambda_{max}^{em}$ (nm) | Molar extinction coefficient $\epsilon$ (M$^{-1}$·cm$^{-1}$) | Quantum Yield $\phi_f$ (CH$_3$OH) |
|---|---|---|---|---|
| 4,4-difluoro-4-bora-1,3,5,7-tetramethyl-8-(5-bromopentyl)-3a,4a-diaza-s-indacene | 495 | 502 | 89600 | 0.98 |
| 4,4-dimethoxy-4-bora-1,3,5,7-tetramethyl-8-(5-bromopentyl)-3a,4a-diaza-s-indacene | 497 | 504 | 54400 | 0.91 |

TABLE 2

| Sequence | Observed (Da) | Calculated (Da) |
|---|---|---|
| A | 3374.7 | 3375.1 |
| B | 6438.9 | 6439.1 |

What is claimed is:

1. A compound of Formula I:

(I)

wherein

X and Y are independently selected from halogen, OH, $C_{1-20}$alkyl, $C_{2-20}$alkenyl, $C_{2-20}$alkynyl, $C_{1-20}$alkoxy, $C_{2-20}$alkenyloxy, $C_{2-20}$alkynyloxy, $C_{3-20}$cycloalkyl, $C_{3-20}$cycloalkoxy, $C_{6-20}$aryl and $C_{6-20}$aryloxy;

$R^1$, $R^2$, $R^3$, $R^4$, $R^5$ and $R^6$ are independently selected from H, halogen, OPg, $C_{1-20}$alkyl, $C_{2-20}$alkenyl, $C_{2-20}$alkynyl, $C_{3-20}$cycloalkyl, heteroaryl, heterocyclyl and $C_{6-20}$aryl, or any two adjacent $R^1$, $R^2$, $R^3$, $R^4$, $R^5$ and $R^6$ groups are joined together to form a 3-20 membered ring system;

Pg is a suitable protecting group;

$R^7$ is selected from $C_{1-20}$alkyl and $(CH_2)_2CN$;

$R^8$ and $R^9$ are independently selected from $C_{1-20}$alkyl and $C_{3-20}$cycloalkyl;

Z is selected from $C_{1-20}$alkylene and $C_{6-24}$arylene; and each alkyl, alkenyl, alkynyl, cycloalkyl, aryl, heteroaryl and heterocyclyl, alone or part of another group, and the ring system, is unsubstituted or substituted with one or more substituents independently selected from halogen, OPg, $C_{1-6}$alkyl, $C_{1-6}$alkoxy and $C_{6-10}$aryl, or a salt or solvate thereof.

2. The compound of claim 1, wherein X and Y are independently selected from halogen and $C_{1-10}$alkoxy, where the alkoxy group is optionally fluoro-substituted.

3. The compound of claim 2, wherein X and Y are both F or are both methoxy.

4. The compound of claim 1, wherein $R^1$, $R^2$, $R^3$, $R^4$, $R^5$ and $R^6$ are independently selected from H, halogen and $C_{1-10}$alkyl, or any two adjacent $R^1$, $R^2$, $R^3$, $R^4$, $R^5$ and $R^6$ groups are joined together to form a 5-6-membered ring, where the alkyl and alkoxy groups are optionally fluoro-substituted.

5. The compound of claim 4, wherein $R^1$, $R^3$, $R^4$ and $R^6$ are independently selected from methyl, trifluoromethyl, ethyl and pentafluoroethyl and $R^2$ and $R^5$ are both H.

6. The compound of claim 1, wherein $R^7$ is $C_{1-6}$alkyl or $(CH_2)_2CN$.

7. The compound of claim 6, wherein $R^7$ is methyl or $(CH_2)_2CN$.

8. The compound of claim 1, wherein $R^8$ and $R^9$ are independently $C_{1-8}$alkyl that is optionally fluoro-substituted.

9. The compound of claim 8, wherein $R^8$ and $R^9$ are independently selected from are both methyl, trifluoromethyl, ethyl or pentafluoroethyl.

10. The compound of claim 1, wherein Z is selected from $C_{1-10}$alkylene and phenylene, and is unsubstituted or substituted with OPg wherein Pg is an acid labile protecting group.

11. The compound of claim 10, wherein Z is $C_{3-8}$alkylene.

12. The compound of claim 1, wherein one of $R^1$, $R^2$, $R^3$, $R^4$, $R^5$ and $R^6$ is OPg and Pg is an acid labile protecting group.

13. The compound of claim 1, selected from:

I(a)

14. The compound of claim 1, that is:

15. A method of labeling an oligonucleotide comprising performing phosphoramidite-based solid phase synthesis of the oligonucleotide wherein at least one of the reactants is a compound of claim 1.

16. A method of labeling an oligonucleotide comprising performing phosphoramidite-based solid phase synthesis of the oligonucleotide wherein at least one of the reactants is a compound of claim 4.

17. A method of labeling an oligonucleotide comprising performing phosphoramidite-based solid phase synthesis of the oligonucleotide wherein at least one of the reactants is a compound of claim 7.

18. A method of labeling an oligonucleotide comprising performing phosphoramidite-based solid phase synthesis of the oligonucleotide wherein at least one of the reactants is a compound of claim 10.

19. A method of labeling an oligonucleotide comprising performing phosphoramidite-based solid phase synthesis of the oligonucleotide wherein at least one of the reactants is a compound of claim 12.

20. A method of labeling an oligonucleotide comprising performing phosphoramidite-based solid phase synthesis of the oligonucleotide wherein at least one of the reactants is a compound of claim 13.

* * * * *

UNITED STATES PATENT AND TRADEMARK OFFICE
CERTIFICATE OF CORRECTION

PATENT NO. : 8,519,153 B2  
APPLICATION NO. : 13/239705  
DATED : August 27, 2013  
INVENTOR(S) : Hongbin Yan et al.

Page 1 of 1

It is certified that error appears in the above-identified patent and that said Letters Patent is hereby corrected as shown below:

In the Claims:

Column 18, line 46, "$C_{1-8}$alkyl" should read --"$C_{1-6}$alkyl"--.

Signed and Sealed this  
Twenty-seventh Day of May, 2014

Michelle K. Lee  
*Deputy Director of the United States Patent and Trademark Office*